United States Patent
Zwaschka et al.

(10) Patent No.: US 9,123,985 B2
(45) Date of Patent: Sep. 1, 2015

(54) POLYHEDRAL PHYSICAL AND ATHLETIC TRAINING MODULE, METHODS OF MAKING AND USING THE SAME, AND COACHING AND TRAINING SYSTEMS INCLUDING THE SAME

(71) Applicant: California State University Fresno, Fresno, CA (US)

(72) Inventors: Brian Zwaschka, Clovis, CA (US); Barry Velasquez, Clovis, CA (US)

(73) Assignees: California State University, Fresno, Fresno, CA (US); Brian Zwaschka, Clovis, CA (US); Barry Velasquez, Clovis, CA (US)

( * ) Notice: Subject to any disclaimer, the term of this patent is extended or adjusted under 35 U.S.C. 154(b) by 203 days.

(21) Appl. No.: 13/839,152

(22) Filed: Mar. 15, 2013

(65) Prior Publication Data
US 2014/0277629 A1 Sep. 18, 2014

(51) Int. Cl.
*G07F 17/32* (2006.01)
*H01P 11/00* (2006.01)

(52) U.S. Cl.
CPC ........... *H01P 11/00* (2013.01); *Y10T 29/49018* (2015.01)

(58) Field of Classification Search
USPC ........................................................ 700/91
See application file for complete search history.

(56) References Cited

U.S. PATENT DOCUMENTS

| 3,811,677 | A | 5/1974 | Saladrigas |
| 4,577,865 | A | 3/1986 | Shishido |
| 5,810,685 | A | 9/1998 | Willner |
| 6,157,898 | A | 12/2000 | Marinelli |
| 6,746,247 | B2 * | 6/2004 | Barton ......................... 434/247 |
| 8,036,826 | B2 | 10/2011 | MacIntosh et al. |
| 2014/0031703 | A1 * | 1/2014 | Rayner et al. ................. 600/484 |
| 2014/0228649 | A1 * | 8/2014 | Rayner et al. ................. 600/301 |
| 2014/0336796 | A1 * | 11/2014 | Agnew ............................. 700/91 |

* cited by examiner

*Primary Examiner* — Pierre E Elisca
(74) *Attorney, Agent, or Firm* — Grace Liu, Esq.

(57) ABSTRACT

A training module, training system, and methods of monitoring physical activity and making a training module are disclosed. The training module includes a compressible article having a polyhedral outer surface, a motion detector that detects compressive and rotational movement of the compressible article, a controller that determines a number of compressions and a number of rotations of the compressible article, and a signal transmitter that transmits data to a mobile electronic device. The controller is in electrical communication with the motion detector and the signal transmitter. The training system and methods generally include those that embody one or more of the inventive concepts disclosed herein. The training module can improve a user's agility, endurance, speed, reflexes, and sensitivity, provide real-time and historical feedback on performance, and improve safety during training in group activities indoors and outdoors, and on a variety of surfaces, that might otherwise involve one or more spherical objects.

20 Claims, 8 Drawing Sheets

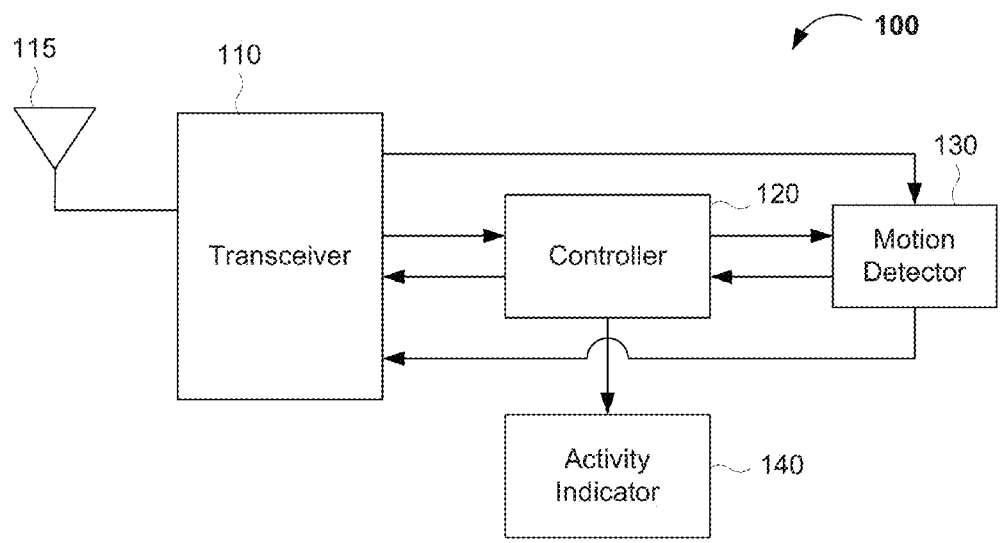
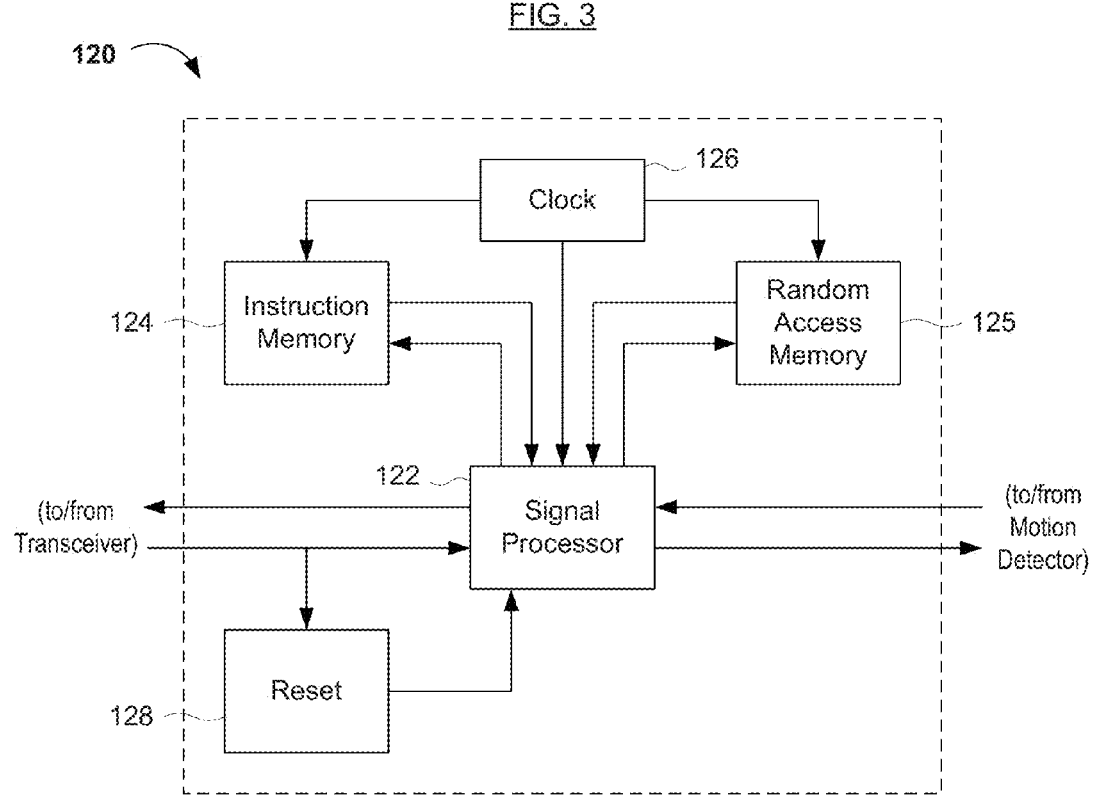

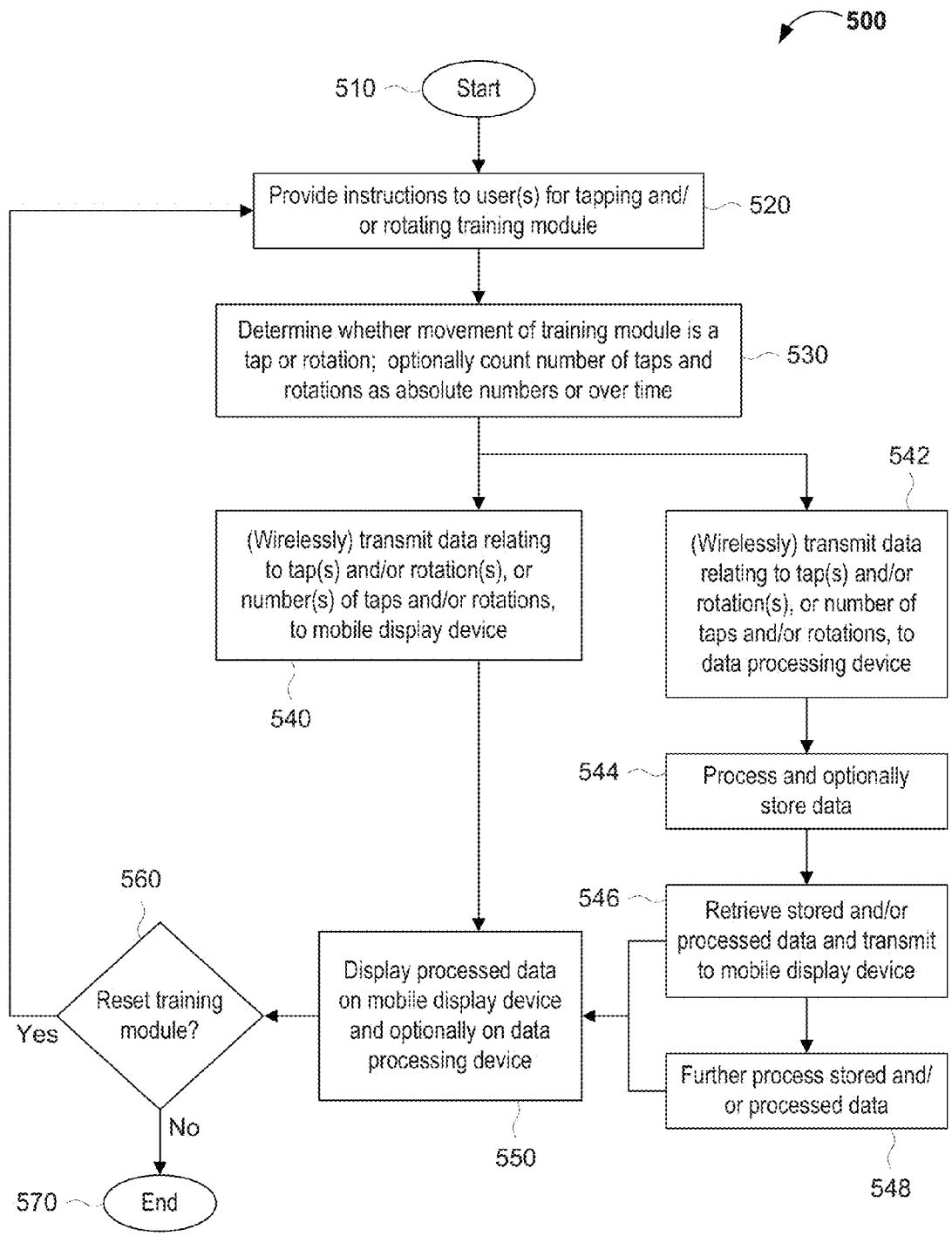

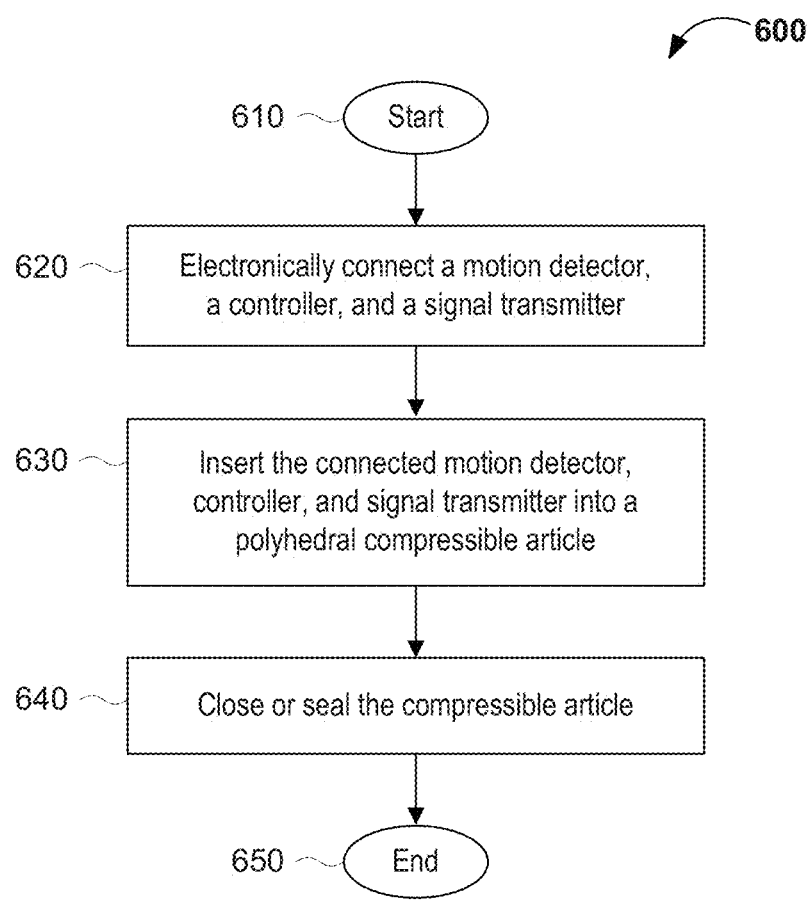

POLYHEDRAL PHYSICAL AND ATHLETIC TRAINING MODULE, METHODS OF MAKING AND USING THE SAME, AND COACHING AND TRAINING SYSTEMS INCLUDING THE SAME

FIELD OF THE INVENTION

The present invention generally relates to the field of fitness and athletic training equipment and programs. More specifically, embodiments of the present invention pertain to a polyhedral physical fitness and athletic training module, methods for making and using the same, and coaching and training systems including the same.

BACKGROUND OF THE INVENTION

Under certain regulations in intercollegiate (e.g., NCAA) athletics, teams may be limited in the number of hours in which they can use certain equipment. For example, in soccer, NCAA rules limit the number of hours per week that an athlete can practice using an actual soccer ball. The game of soccer requires footwork training which is difficult to replicate without a soccer ball. Accordingly, a need is felt for training equipment that mimics or replicates footwork skills that can be practiced and/or perfected without using a soccer ball.

Similarly, certain drills or repetitive exercises can be performed to enhance one's agility and/or hand-eye or foot-eye coordination. However, it is not always possible to get real-time data on performances of such drills or exercises, and analysis of performance over time may be even more lacking. In addition, in team sports or group activities, where there may be many users in a relatively confined space, and use of spherical or substantially spherical objects as training tools introduces a safety hazard for the users. They may not see or recognize when a nearby user loses control of the object, which can roll into the path or training area of another user, who can inadvertently step on the object and lose their balance. While this risk is present outdoors and indoors, it is particularly high indoors, where walls and other surfaces constrain available space and increase the probability of a ricochet or deflected ball creating a safety issue.

Also, fitness enthusiasts continually seek new and more interesting challenges for improving one's fitness, strength, endurance and/or agility. Real-time feedback is important to fitness enthusiasts who seek such information to determine the effectiveness of a particular fitness regimen.

Finally, physical therapists are continually looking for tools and techniques for improving agility and/or strength of certain muscles or muscle groups in patients in need of such strength and/or conditioning therapy. Often, games involving physical activity are effective in assisting those in need of therapy to improve agility and/or strength of certain muscles or muscle groups.

SUMMARY OF THE INVENTION

Embodiments of the present invention relate to a training module, a training system, and methods of monitoring physical activity and making a training module. The training module generally comprises a compressible article having a polyhedral outer surface, and a motion detector, a controller, and a signal transmitter in the compressible article. The motion detector is generally configured to detect compressive and rotational movement of the compressible article. The controller is in electrical communication with the motion detector, and is generally configured to determine a number of compressions and a number of rotations of the compressible article. The signal transmitter is in electrical communication with the controller, and is generally configured to transmit data (e.g., to a mobile electronic device or other signal receiving device in a network) regarding the number of compressions and/or rotations of the compressible article.

Typically (but not always), the polyhedral outer surface of the compressible article has the shape of a regular or semi-regular polyhedron having at most 12 sides. In the present application, a "semi-regular" polyhedron is an object or article having outer surfaces consisting of regular polygonal shapes (e.g., a triangle, square, rectangle, pentagon, hexagon, etc.).

In some embodiments of the training module, the motion detector comprises an accelerometer and/or a gyroscope in communication with the controller. Optionally, the motion detector comprises or further comprises one or more pressure sensors in electrical communication with the controller.

In some embodiments of the training module, the signal transmitter comprises a wireless signal transmitter and an antenna. Additionally or alternatively, the training module further comprises a battery providing electrical power to the controller, the motion detector, and the signal transmitter, and optionally, a switch configured to disconnect the battery from the controller. In further embodiments, the training module further comprises an activity monitor configured to indicate when the motion detector and/or the signal transmitter are active.

In further embodiments of the training module, the controller comprises a signal processor, one or more memories, and a clock circuit. The signal processor is generally configured to communicate electrically with the motion detector and the signal transmitter. The memory(ies) is/are generally configured to store instructions and/or data. The clock circuit is generally configured to provide a timing signal to the signal processor, and optionally, to at least one of the memory(ies). For example, one memory (e.g., a nonvolatile memory, such as a read-only memory or flash memory) may store an instruction set configured to determine whether a movement of the motion sensor in one dimension is a compression; determine whether a movement of the motion sensor in two dimensions is a rotation of the compressible article, and transmit a data signal to an external electronic device when the compression or the rotation occurs. The compression may be, for example, a foot tap on a top surface or on one of at least two side surfaces of the compressible article. The controller may further comprise a reset circuit configured to reset the signal processor, and optionally, to erase at least one of the memory(ies).

In another aspect of the present invention, the training system generally comprises the present training module (or other training module embodying one or more of the inventive concepts disclosed herein) and a mobile electronic device, configured to display a number of compressions and a number of rotations of the compressible article. The training system may further comprise a data storage unit configured to store compression and rotation data from the training module, and/or a computer configured to process the compression and rotation data and display information relating to one or more summaries of and/or trends in the compression and rotation data. In further embodiments, the training system further comprises a second training module and a second mobile electronic device. In some of these embodiments, the computer is capable of (i) simultaneously receiving data from the first and second training modules in real time and (ii) processing the compression and rotation data from each of the first and second training modules.

In a further aspect of the present invention, the method of monitoring physical activity generally comprises (1) instructing one or more users to tap and/or rotate a training module associated with a unique user, collecting data relating to a number of compressions on a surface of the compressible article and/or a number of rotations of the training module, and displaying to the user on a mobile electronic device the number of compressions and the number of rotations of the training module. The training module in this method is generally the present training module (e.g., comprising a compressible article having a polyhedral outer surface, a motion detector configured to detect compressive and rotational movement of the compressible article, a controller in electrical communication with the motion detector and configured to determine a number of compressions and a number of rotations of the compressible article, and a signal transmitter in electrical communication with the controller and configured to transmit data regarding the number of compressions and/or rotations of the compressible article to an external electrical device having a display thereon or therein).

In some embodiments of the method of monitoring physical activity, the user is instructed to (i) tap the training module a first predetermined or minimum number of times and (ii) rotate the training module a second predetermined or minimum number of times, all within a predetermined period of time. For example, the user may be instructed to tap a first surface of the training module the first predetermined or minimum number of times, rotate the training module in a first direction the second predetermined or minimum number of times; rotate the training module in a second direction a third predetermined or minimum number of times; tap a second surface of the training module a fourth predetermined or minimum number of times; tap a third surface of the training module a fifth predetermined or minimum number of times; and/or rotate the training module in a third direction a sixth predetermined or minimum number of times.

Similar to the present training module, the method may further comprise storing instructions to determine the number of compressions and the number of rotations of the compressible article in one or more memories, and/or display the number of compressions and the number of rotations of the compressible article to the user on the mobile electronic device. Optionally, the instructions may include an instruction to display commands or indications on the mobile electronic device to tap the first surface of the training module and/or rotate the training module (for example, at certain times or in a certain sequence, optionally within a predetermined period of time). The method and/or instructions may consider the first surface of the training module to be a top surface, the first direction to be a first panel or side of the polyhedral compressible article to the right, and the second direction to be one panel or side of the polyhedral compressible article to the left.

Further embodiments of the method of monitoring physical activity may further comprise transmitting the data relating to the number of compressions on the surface of the compressible article and/or the number of rotations of the compressible article to a data processing device. The data processing device may process the data and/or store the data (processed or unprocessed) in a data storage unit. Optionally, the method of may further comprise retrieving the processed or unprocessed data from the data storage unit, further process the processed or unprocessed data, and/or display the (further) processed or unprocessed data on the mobile electronic device.

In embodiments involving multiple training modules, the method may further comprise instructing a plurality of users to tap and/or rotate a training module associated with a unique user, collecting data relating to the number of compressions and/or the number of rotations from the associated training modules in real time; displaying to each of the users on an associated mobile electronic device the number of compressions and the number of rotations of the associated compressible article; processing the compression and rotation data from each of the plurality of training modules; and/or displaying the processed data on a display receiving an output from a processing device that processes the compression and rotation data.

According to a further aspect of the present invention, the method of making a training module generally comprises assembling a motion detector, a controller, and a signal transmitter into a motion detecting and data transmitting circuit, inserting the motion detecting and data transmitting circuit in the compressible article; and closing or sealing the compressible article. Assembling the motion detecting and data transmitting circuit generally comprises electrically connecting the motion detector, controller, and signal transmitter such that the motion detector is configured to detect compressive and rotational movement of a compressible article having a polyhedral outer surface, the controller is configured to determine a number of compressions and a number of rotations of the compressible article, and the signal transmitter is configured to transmit data regarding the number of compressions and/or rotations of the compressible article. In some embodiments, the method of making the training module may further comprise inserting a battery into the compressible article and connecting the battery to at least the controller (and optionally to one or more of the motion detector, the signal transmitter, and a switch configured to disconnect the battery from the motion detecting and data transmitting circuit). In additional or alternative embodiments, the signal transmitter comprises a wireless signal transmitter.

These and other aspects of the present invention will become readily apparent from the detailed description of various embodiments below.

BRIEF DESCRIPTION OF THE DRAWINGS

FIG. 2 is a block diagram of an exemplary circuit suitable for the present training module.

FIG. 3 is a block diagram of an exemplary controller architecture suitable for the exemplary circuit of FIG. 2.

FIG. 8 is a flow chart for an exemplary method of monitoring physical activity in accordance with an aspect of the present invention.

FIG. 9 is a flow chart for an exemplary method of making a training module in accordance with another aspect of the present invention.

DETAILED DESCRIPTION

Figure 1A:
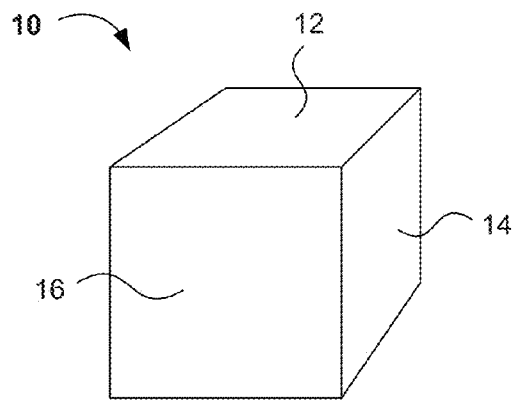
FIGS. 1A-1E show exemplary polyhedral shapes suitable for the present compressible article.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The invention involves a training module comprising a compressible article having a polyhedral outer surface. In one embodiment, the compressible article comprises a polyhedron-shaped piece of foam material (e.g., a foam cube) approximating the dimensions of certain athletic equipment (having a size of 8 in.×8 in.×8 in. similar to those of a soccer ball). The player can use the polyhedron (e.g., the foam cube) to perform the following drills:

1. Alternating left and right foot sole taps on the top surface or plane of the polyhedron (e.g., the foam cube).
2. Alternating left and right inside foot taps on side surfaces or planes of the polyhedron (e.g., the left and right sides of the foam cube) to roll the polyhedron over (e.g., 90 degrees) to an adjacent plane or side of the polyhedron.
3. Running shuttle runs starting and stopping with a foot sole tap on the top surface or plane of the polyhedron (e.g., of the foam cube).
4. Holding the polyhedron (e.g., the foam cube) between the ankles and broad jumping.
5. Holding the polyhedron (e.g., the foam cube) between the ankles and vertical jumping.

Currently, at least one NCAA athletic team uses foam cubes (without internal electronics) to do all of the above drills. The training cube has many uses, including practicing soccer drills by players of all levels, for NCAA soccer teams to comply with intercollegiate athletics regulations, for track and field athletes to practice certain agility drills, for fitness enthusiasts to conduct agility, speed and endurance exercises, for physical therapy to assist patients in recovering from injury or medical treatment, etc. The training sport cube can be synchronized with and/or into computers and mobile phones so that athletes can readily upload training regimens and review practice and/or exercise data.

The training cube includes an embedded electronic processing unit to count cube movements (e.g., compressions resulting from foot sole taps and cube plane rotations), optionally over time or as a function of time. By including the electronic components, users are not required to manually or mentally count each of the movements of the polyhedron (or have another person manually or mentally count such movements), and can concentrate more on the drills or exercises. Also, the drills are more objectively quantified, and not subject to human counting or timing errors.

The compressible polyhedron (e.g., a foam cube) may have a cavity therein for an electronic device to be inserted. The electronic device communicates wirelessly with and can be detected by mobile electronic devices, such as smart phones, cell phones, and laptop computers. Such mobile electronic devices are configured to record the movements and rotations of the compressible polyhedron (e.g., along the X, Y, and Z axes of the polyhedron). Following programming and user calibration, the compressible polyhedron (e.g., the foam cube) determines how many compressions (e.g., taps on) and rotations of the polyhedron occur, and the mobile electronic device counts the movements (e.g., compressions and rotations) along each axis or degree of freedom.

The design of the circuit board and components in the electronic device is described below and shown in the Figures. One novel aspect of the invention is that it provides an athletic training device that counts the number of discrete compressions (e.g., touches) and rotations of a polyhedral object. The training device is not intended for use in athletic competitions, although it is possible that athletic competitions can be conducted using the present training module and system. There is no training module or system known to the present inventors that includes motion detectors such as accelerometers and gyroscopes within polyhedral (e.g., planar) devices to count discrete touches and rotations.

The present invention includes an athletic skill and/or training device comprising an object having planes (e.g., a compressible polyhedral object), an electronic processing unit embedded or included in the object, wherein the electronic processing unit measures discrete contacts with the planes and rotations of the object. The invention, in its various aspects, will be explained in greater detail below with regard to exemplary embodiments.

Exemplary Training Modules

In one aspect, the present invention relates to a training module, comprising a compressible article having a polyhedral outer surface; a motion detector in the compressible article, configured to detect compressive and rotational movement of the compressible article; a controller in the compressible article, in electrical communication with the motion detector, configured to determine a number of compressions and a number of rotations of the compressible article; and a signal transmitter in the compressible article, in electrical communication with the controller, the signal transmitter configured to transmit data regarding the number of compressions and/or rotations of the compressible article.

FIGS. 1A-1E show exemplary embodiments of polyhedrons suitable for use in the present invention. In general, the polyhedron is made of a compressible material, such as rubber, a solid foam, an air- or gas-filled plastic, a lightweight material such as balsa wood, combinations thereof, etc. While the compressible material is generally lightweight, it may be of any density, to allow for various degrees of training challenges or complexity. FIG. 1A shows a first embodiment of the training module in the shape of a cube 10. The cube 10 can have any dimensions so that the cube 10 can be compressed and rotated without undue force or facile "false positive" movements, which can be caused by external and/or uncontrolled forces such as wind, vibration from movement of the ground or floor caused by the user or other people, etc. For example, each surface or side (e.g., top side 12, right side 14, front side 16, etc.) may have dimensions of from 10 cm×10 cm (4 in.×4 in.) to 30 cm×30 cm (12 in.×12 in.). In one example, the cube 10 has sides or surfaces 12, 14, 16 that are 20 cm×20 cm (8 in.×8 in.).

The training cube 10 is configured to count or track certain movements of the cube, performed as part of an exercise, physical therapy or training regimen. For example, the cube 10 generally counts or tracks the number of compressions (e.g., foot taps) and rotations (e.g., onto side 14) of the cube. In one instance, the cube 10 counts the number of times that the top surface 12 is tapped or compressed by the user's foot. The cube 10 can be configured in at least two ways: to count the number of surface taps without regard to the user's left or right foot, or to count the number of taps by the user's left foot vs. the user's right foot. Generally, the cube 10 will not determine whether the user's right foot or left foot tapped the cube 10, but in one embodiment, one or more sensors can be placed in the cube 10 below the top surface 12 in each of the right half and left half of the cube 10, and the user can be instructed that a tap on the right half of the top surface 12 is counted as a tap with the right foot, and a tap on the left half of the top surface 12 is counted as a tap with the left foot.

Similarly, the cube 10 counts or tracks the number of planar rotations of the cube. Generally, one planar rotation can be considered one turn. In one instance, the user taps the cube 10 on the right side 14 with sufficient force to cause the cube 10 to rotate one turn (or 90°) to the left. Also, the user can tap the cube 10 on the left side (not shown) to cause the cube 10 to rotate one turn (or 90°) to the right, onto side surface 14. Generally, the cube 10 will not determine whether the user's right foot or left foot caused the cube 10 to rotate, but in one embodiment, instructions can be provided to both the user and to data processing software to identify which foot is to strike the cube and cause the rotation before the user rotates the cube with the identified foot. After the cube 10 rotates, a new side or surface becomes the top surface 12, and depending on whether the cube 10 was rotated to the right, left, or back, one or more new sides or surfaces will become the front side (if the cube 10 is rotated back) or the right and left sides (if the cube 10 is rotated to the right or left).

In some embodiments, the cube 10 counts or tracks the number of compressions and/or rotations over time. The length of time may be either a predetermined period of time (e.g., 5 seconds, 10 seconds, 30 seconds, 1 minute, 2 minutes, 5 minutes, 10 minutes, etc.), or a timed or counted length (e.g., the length of time needed to tap the top surface 12 of the cube 10 times, 20 times, etc., and/or to rotate the cube to the right 5 times, to the right 5 times and to the left 5 times, to the left 10 times, or multiples and/or combinations thereof).

Figure 1B:
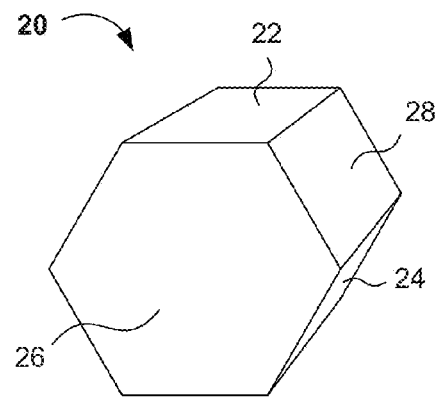

FIGS. 1B-1E show additional embodiments of compressible polyhedrons suitable for use in the present training module. For example, FIG. 1B shows a compressible polyhedron 20 with 8 sides: a hexagonal front side 26 and corresponding hexagonal back side (not shown), and six (6) square or rectangular sides (e.g., top side or surface 22, lower right side or surface 24, and upper right side or surface 28). In this case, because the compressible polyhedron 20 has sides or surfaces consisting of different regular polygonal shapes (e.g., hexagons and squares or rectangles), it may be considered to be a "semi-regular" polyhedron. Other semi-regular polyhedrons may have sides with more than two different regular polygonal shapes, and the regular polygonal shapes may be triangular, square, rectangular, pentagonal, hexagonal, octagonal, etc.

Referring to FIG. 1B, when the front side 26 of the semi-regular polyhedron 20 is facing the user, compressions can be counted or tracked on the top side 22, upper right side 28, and upper left side (not shown) of the 8-sided compressible polyhedron 20. If the side surfaces 24 and 28 are facing the user, compressions on the hexagonal front side 26 and back side (not shown) can be counted or tracked. Similarly, when the front side 26 is facing the user, rotations to the right (e.g., onto lower right side 24) and left (e.g., onto the lower left side; not shown) can be tracked, and when side surfaces 24 and 28 are facing the user, rotations to the left (e.g., onto front side 26) and right (e.g., onto the back side; not shown) can be tracked. The semi-regular polyhedron 20 can be advantageously used to improve the user's sensitivity, in that rotations of 60°, 90°, and even 120° (i.e., two rotations to the left or right when front side 26 is facing the user) can be counted and/or tracked. The semi-regular polyhedron 20 may have dimensions similar to those of the cube 10 in FIG. 1A. For example, the square or rectangular polygons (e.g., surfaces 22, 24 and 28) may have independent length and width dimensions of from 10 cm (4 in.) to 30 cm (12 in.), but generally, the length and width of each square or rectangular will be similar to each other (e.g., within 25-35% of each other).

Figure 1C:
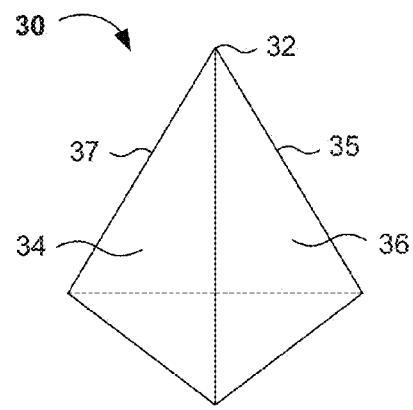

FIG. 1C shows a 4-sided pyramidal polyhedron 30 that can be similarly used for training. For example, the polyhedron 30 generally counts or tracks the number of compressions and rotations of the polyhedron. In one instance, the polyhedron 30 counts the number of times that the top 32, and optionally the front left side 34 and/or front right side 36, is tapped or compressed by the user's foot. Also, the polyhedron 30 counts rotations to the left when the user hits the right edge 35 of polyhedron 30 with sufficient force to cause the polyhedron 30 to rotate one turn (or 120°) onto its front left side 34, and rotations to the right when the user hits the left edge 37 of polyhedron 30 with sufficient force to cause the polyhedron 30 to rotate one turn (or 120°) onto the front right side 36. The pyramidal polyhedron 30 is advantageous in that it is less likely to continue rotating in the event of excess force being applied to it, and thus improve, optimize or maximize a safety feature of the present training module. The pyramidal polyhedron 30 may have dimensions similar to those of the cube 10 in FIG. 1A, but may advantageously be in the smaller end of the range (e.g., it may have a height of from 10 cm [4 in.] to 15 cm [6 in.]).

Figure 1D:
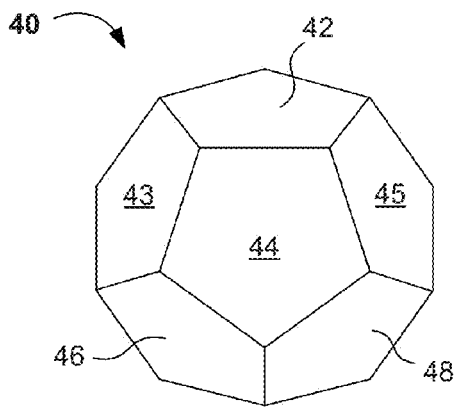

FIG. 1D shows a compressible dodecahedron 40, suitable for use in the present training module. Similar to other compressible polyhedrons, dodecahedron 40 counts or tracks the number of compressions and rotations of the polyhedron. In one instance, the dodecahedron 40 can count the number of times that the top side or surface 42, and optionally the upper left front side 43, upper front side 44 and/or upper right front side 45, is tapped or compressed by the user's foot. Also, the dodecahedron 40 can count rotations in any of up to five (5) different directions. For example, when the user hits the upper right front side 45 with sufficient force, the dodecahedron 40 rotates one turn (approximately 72°) onto its lower left back side (not shown). Similarly, striking the upper left front side 43 with sufficient force causes the dodecahedron 40 to rotate one turn (approximately 72°) onto its lower right back side (not shown). The dodecahedron 40 is advantageous in that its behavior approximates that of a soccer ball, while maintaining sufficiently large flat surfaces to minimize the likelihood that the polyhedron might continue rotating in the event of excess force being applied to it, and thus maintain the safety feature(s) of the present training module. Dodecahedron 40 may have dimensions similar to those of the cube 10 in FIG. 1A, but may advantageously be in the larger end of the range (e.g., it may have a height of from 20 cm [8 in.] to 30 cm [12 in.]).

Figure 1E:
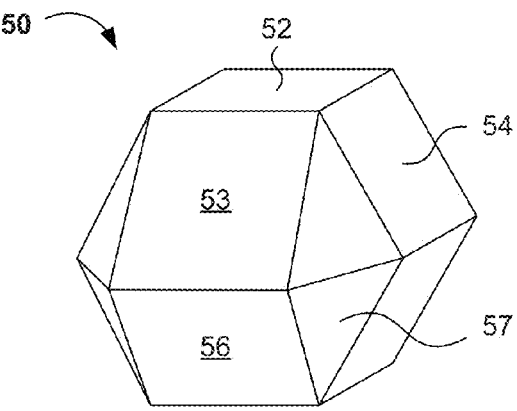

FIG. 1E shows a compressible semi-regular, 18-sided polyhedron 50, suitable for use in the present training module. Similar to other compressible polyhedrons, polyhedron 50 counts or tracks the number of compressions and rotations of the polyhedron. In one instance, the polyhedron 50 can count the number of times that the top side or surface 52, upper left side (not shown), upper front side 53 and/or upper right side 54 is tapped or compressed by the user's foot. Also, the polyhedron 50 can count rotations in generally up to four (4) different directions. For example, when the user hits the upper right side 54 with sufficient force, the dodecahedron 40 rotates one turn (approximately 60°) onto its lower left side (not shown). Similarly, placing the foot on the top surface 52 and pulling the polyhedron 50 with sufficient force causes the polyhedron 50 to rotate one turn (approximately 60°) onto its lower front side 56. Triangular surfaces (e.g., 57) may be too small or unstable for reliable rotational measurements onto them. Polyhedron 50 may have dimensions similar to those of the dodecahedron 40 in FIG. 1D.

At some point, the number of sides on the training module approaches a sphere, which may be in violation of certain regulations in intercollegiate or amateur athletics, and which may reduce or substantially eliminate the safety benefit(s) of the present training module. Also, the conditioning and/or therapeutic benefit of the present training module may be lost as the compressible polyhedron acquires characteristics of a sphere. Thus, in the present training module, the polyhedral outer surface of the compressible polyhedron advantageously has the shape of a regular polyhedron having at most 12 sides or a semi-regular polyhedron having at most 18 sides.

Referring now to FIG. 2, the present training module generally includes a motion detecting and data transmitting circuit 100 in the compressible article, the circuit 100 comprising a motion detector 130 (e.g., an accelerometer and/or gyroscope), a controller 120, and a signal transmitter (e.g., transceiver 110). Although only the signal transmitting function of the transceiver 110 is required for operation of the present training module, to the extent that it is advantageous for the training module to receive information and/or be programmed, the signal transmitter may comprise the transmitter portion of the transceiver 110. The circuit 100 is configured to detect compressive and rotational movement of the compressible article, determine a number of compressions and a number of rotations of the compressible article, and transmit data regarding the number of compressions and/or rotations of the compressible article. The controller 120 is generally in electrical communication with the motion detector 130, and the signal transmitter (e.g., transceiver 110) is generally in electrical communication with the controller 120.

The motion detector 130 may be configured to measure information or data for up to six degrees of freedom (6DOF); i.e., along orthogonal x-, y- and z-axes (height, length, and depth; alternatively, moving up and down, left and right, and forward and backward), and along orthogonal rotational axes (i.e., roll, pitch and yaw). This information or data is used to determine the position of the training module. In some embodiments, the motion detector 130 comprises an accelerometer and/or a gyroscope in communication with the controller 120. In some cases, the accelerometer may be or comprise a microelectromechanical system (MEMS) that determines motion in one or more directions by measuring a change in electrical capacitance resulting from a change in the position of a mechanical object in the accelerometer. The gyroscope may also be or comprise be a microelectromechanical system (MEMS). Typically, one accelerometer is used for each dimension of movement to be detected. However, a gyroscope generally determines all three types of rotational motion (roll, pitch and yaw). Optionally, the motion detector 130 comprises (or further comprises) one or more pressure sensors in electrical communication with the controller.

In general, a single accelerometer may be sufficient for the motion detector 130. It may be placed in or near the center of the training module, and as long as it provides information for at least the three (3) orthogonal linear degrees of freedom (e.g., along the x-, y- and z-axes), compressions and rotations can be detected and reported. Alternatively, a gyroscope (to determine orthogonal angular degrees of freedom, such as roll, pitch and yaw) and a plurality of pressure sensors (to determine compressions on a corresponding number of surfaces) may be sufficient. A number of additional pressure sensors can help improve the accuracy and/or reliability of the data and/or information from the training module. Ideally, there can be one pressure sensor under each corner of each face of the training module for which compressions and/or rotations are determined and/or measured. Thus, referring back to FIG. 1A, cube 10 may have up to 24 pressure sensors (i.e., one under each of the four corners on each of the six faces of the cube 10). In the embodiment of FIG. 1C, there may be up to 12 pressure sensors (i.e., one under each of the three corners on each of the four faces of the pyramid 30). However, in embodiments with a relatively large number of faces (e.g., 10 or more, 12 or more, etc.), a single pressure sensor under each side or face (e.g., the center of each side or face) may be sufficient. For example, in the dodecahedron 40 of FIG. 1D, a single pressure sensor under the center of each side or face (e.g., surfaces 42-46 and 48) may be sufficient to determine compressions on each surface and rotations of the dodecahedron 40 in any given direction.

The controller 120 (e.g., a central processing unit [CPU]) may be configured to perform data collection, to instruct users as to a given training routine, and to transmit data, information and/or instructions. Controller 120 generally includes logic configured to provide the specified functions. Controller 120 may further provide power to other components of the motion detecting and data transmitting circuit 100.

For example, and referring to FIG. 3, the controller 120 may comprise a signal processor 122, one or more memories 124-125, a clock or timing circuit 125, and a reset circuit 128. The signal processor 122 is configured to communicate electrically with the motion detector 130 (FIG. 2) and the signal transmitter (e.g., transceiver 110 in FIG. 2). The clock circuit 125 is configured to provide a timing signal to the signal processor 122, and optionally, to at least one of the memories 124 and 125.

The reset circuit 128 is configured to reset the signal processor, and optionally, at least one of the one or more memories, generally in response to a reset signal from an external source. In one example, the controller (e.g., an instruction queue) is reset in response to a first reset signal (e.g., to restart the training regimen). This reset signal may be generated by pushing a reset button on the surface of the training module or by touching a reset button in the display of a mobile electronic device (e.g., a smart phone, laptop or tablet computer, etc.) in electrical communication with the training module. The random access memory may be reset or erased in response to the first reset signal or a second reset signal (e.g., to restart the compression or rotation count). Thus, the reset signal received by the reset circuit 128 may be internal (e.g., from an input on or in the training module) or external (e.g., from a mobile electronic device operated by the user or a coach or instructor).

The memories 124-125 may be configured to store instructions (e.g., instruction memory 124) and/or data (e.g., random access memory 125). For example, the instruction memory 124 may store a set of instructions configured to determine whether a movement of the motion sensor in one dimension is a compression on a top surface or on one of at least two side surfaces of the compressible article, determine whether a movement of the motion sensor in two or more dimensions is a rotation of the compressible article, and transmit a data signal to an external electronic device when the compression or the rotation occurs. Additional instructions include resetting the controller (e.g., the instruction queue) in response to a first reset signal (e.g., to restart the training regimen) and/or resetting or erasing the random access memory in response to the first reset signal or a second reset signal (e.g., to restart the compression or rotation count). The instruction memory 124 may include a pointer memory to temporarily store locations or addresses of certain instructions for execution, or the pointer memory may be included in the random access memory 125.

Referring back to FIG. 2, the transceiver 110 may comprise a WiFi module, such as a ZIGBEE-compatible RF module (e.g., an XBEE or XBEE PRO RF module commercially available from Digi International, Minnetonka, Minn.). The transceiver 110 generally includes a wireless signal transmitter configured to transmit data to a monitoring device (e.g., a mobile electronic device, such as a smart phone, laptop or tablet computer, personal digital assistant, etc., programmed with monitoring software). Embedding the transceiver 110 in the training module offers optimal configuration possibilities for data collection and control communications using the training module. For example, WiFi modules are relatively inexpensive, and the communication protocols are ubiquitous. The transceiver 110 supports ad-hoc and infrastructure modes, and the training module may function as an access point or a simple client when equipped with a WiFi-compatible transceiver 110, thereby providing the product designer, the training regimen creator (e.g., coach or instructor), and the user with many options for the network topology and for communication with the training module. Thus, in most embodiments of the training module, the signal transmitter comprises a wireless signal transmitter and an antenna.

It is well within the abilities of one skilled in the art to design and use electrical circuitry and/or logic configured to perform the functions described herein with regard to the circuitry 100 of FIG. 2 and the controller 120 of FIG. 3. For example, FIG. 4 shows an exemplary circuit board design 200 for the motion detecting and data transmitting circuit to be included in the compressible article of the present training module.

Figure 4:
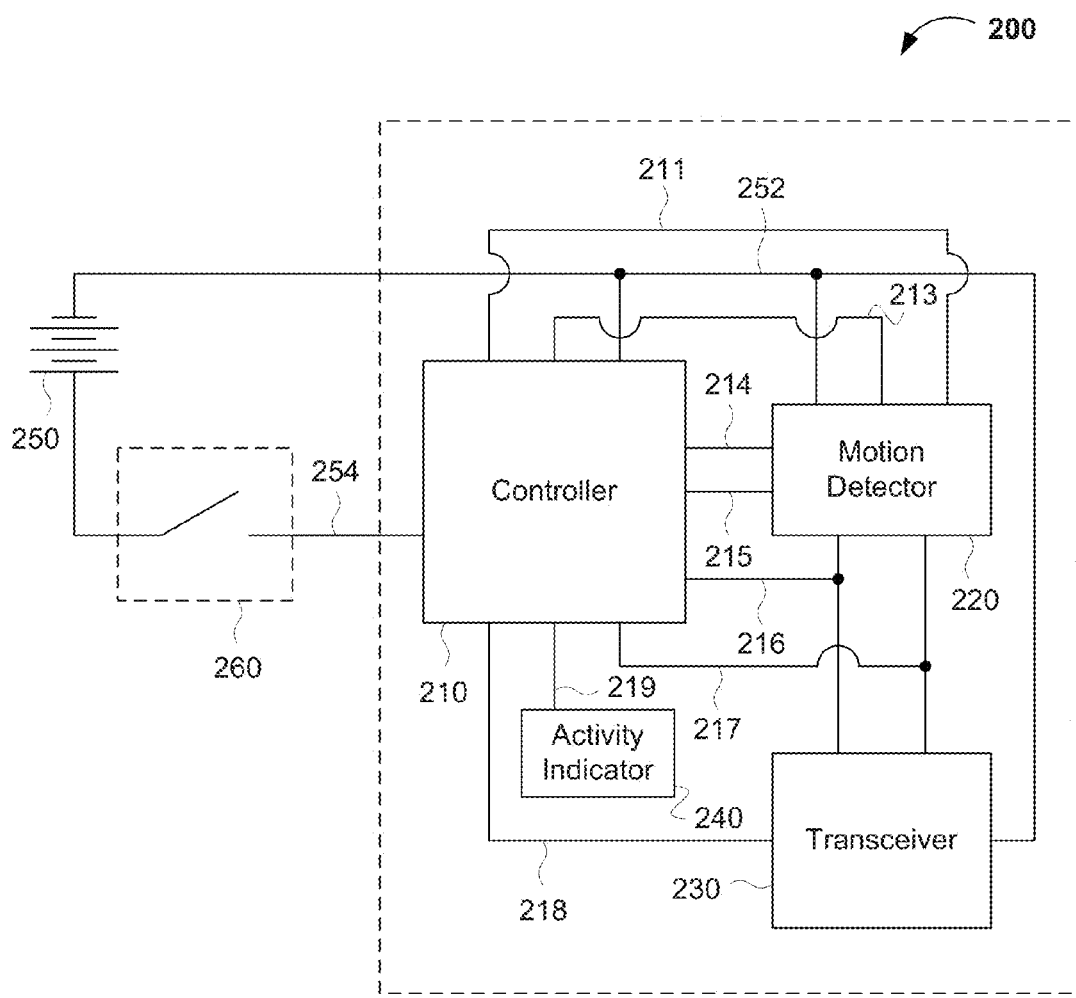
FIG. 4 is an exemplary circuit board design to be included in the present training module.

The motion detecting and data transmitting circuit board 200 of FIG. 4 includes a controller 210, a motion detector 220, a transceiver 230, and an activity indicator 240. To enable fully wireless operation, the training module may include a battery 250, which provides electrical power to the controller 210 and the motion detector 220 over bus 254 when a switch 260 is closed. Optionally, the battery 250 may provide electrical power to the signal transmitter 230. Alternatively, the training module may include a conventional adapter for connecting a power cord that can be plugged into a standard AC electrical outlet. In either case, the training module may further comprise the switch 260, which is configured to connect and disconnect the battery or power supply to and from at least the controller 210.

As shown in FIG. 4, the controller 210 controls substantially all of the operations of the training module. For example, the controller 210 may provide analog and/or digital control signals to the motion detector 220 on control bus(es) 211. In some embodiments, control bus 211 transmits an analog control voltage or bias current to the motion detector 220. In other embodiments, control bus 211 may transmit a reset signal to the motion detector 220.

Controller 210 may receive analog and/or digital information from the motion detector 220 on buses 213, 214 and 215. Typically, the information from the motion detector 220 comprises information from one or more accelerometers and/or a gyroscope relating to compressions and/or the position of the training module.

The transceiver 230 can receive data for transmission to one or more external devices (e.g., a mobile electronic device) from both the controller 210 and the motion detector 220 on bus 217. Bus 217 is generally a serial bus, but in some embodiments, it may be parallel (e.g., multi-bit). The transceiver 230 can transmit data and instructions/commands received from one or more external devices to the controller 210 on bus 218. Similar to bus 217, bus 218 is generally a serial bus, but in some embodiments, it may be parallel (e.g., multi-bit).

The controller 210 receives a supply voltage (e.g., +9V) on power supply line 254 from the battery 250 through switch 260. The controller 210 may provide a regulated voltage (e.g., +5V) to each of the motion detector 220 and transceiver 230 on bus 216. However, any regulated voltage or power supply to be provided to the motion detector 220 and transceiver 230 may be provided by a separate or discrete voltage regulator. A ground bus or plane 252 may be connected between the negative terminal of the battery 250 and each of the controller 210, motion detector 220, and transceiver 230.

The activity monitor 240 is configured to indicate when the motion detector and/or the signal transmitter are active. In one embodiment, the activity monitor 240 receives an activity indication signal from the controller 210 on bus 219. The activity indication signal may be a simple regulated voltage from the controller 210 when power is applied to the controller 210. Alternatively, the activity monitor 240 can receive power directly from the battery 250 or from another component on the circuit board 200, and a digital activity indication signal on the bus 219, for example when the controller 210 is executing instructions. The activity monitor 240 may be visual (e.g., an LED light, which may be intermittent, periodic, or continuous) or auditory (e.g., an intermittent or periodic beeping sound, or a continuous auditory signal, such as music from an on-board MP3 or MP3-like player).

Prior to insertion into the training module, the motion detecting and data transmitting circuit board 200 may be enclosed or encased in a housing configured to protect the circuit board 200 from liquids (such as water) and/or extreme shock. The housing may have openings sufficiently large to allow wires from an external switch (when present) and/or a battery (when housed separately from the circuit board 200) to pass through to the circuit board 200, and to enable the user to view an optical activity monitor or hear an auditory activity monitor. Thus, the battery 250 may be included in the housing or in a separate housing adjacent and/or attached to the housing for the circuit board 200. Enclosing or encasing the battery 250 in a separate housing protects both the battery 250 (e.g., from liquids and extreme shock) and the circuit board 200 (e.g., from possible electrical issues and/or corrosion from the battery 250), and enables facile replacement by the user (e.g., if the housing for the battery is in a separately accessible location on or near the surface of the compressible polyhedron). In one embodiment, the switch 260 may be mounted on the external surface of the housing the circuit board 200, but be wired completely inside the housing containing the circuit board 200.

Exemplary Training Systems

The present training system generally comprises the present training module (or other training module embodying one or more of the inventive concepts disclosed herein) and a mobile electronic device, configured to display a number of compressions and a number of rotations of the compressible article. The present training system may further comprise a data storage unit configured to store compression and rotation data from the training module, and/or a computer configured to process the compression and rotation data and display information relating to one or more summaries of and/or trends in the compression and rotation data. On a multi-user scale, the training system may further comprise the computer, a second training module, and a second mobile electronic device, where the computer is capable of (i) simultaneously receiving data from the first and second training modules in real time and (ii) processing the compression and rotation data from each of the first and second training modules.

Figure 5:
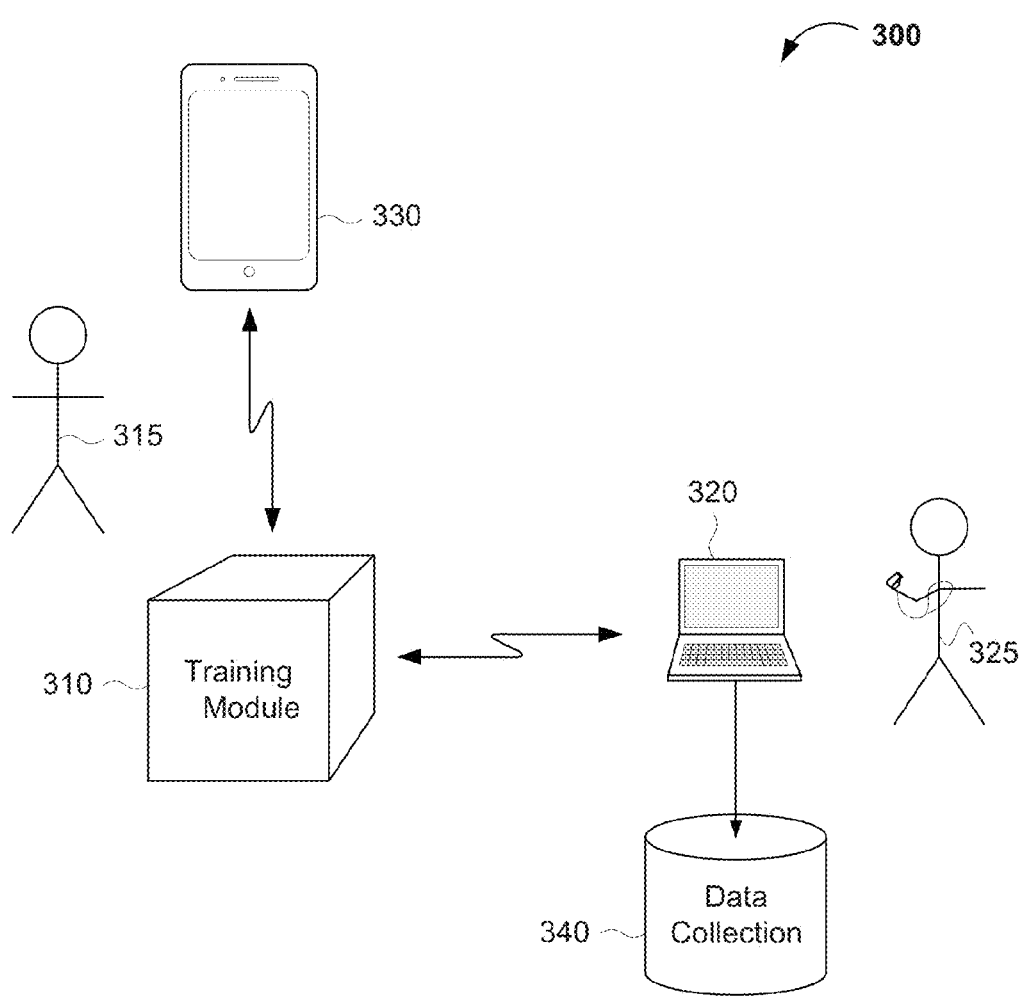
FIG. 5 shows an exemplary training system in accordance with an embodiment of the present invention.

FIG. 5 shows a simple, single-user network 300 comprising the present training module 310, a first mobile electronic device (e.g., laptop 320), and a second mobile electronic device (e.g., smart phone or other smart device 330). The laptop 320 is under the control of an instructor or coach 325, and the smart phone 330 is accessible to and/or under the control of the user 315. The training module 310 functions as an access point and/or as a server in the network 300.

The network 300 connects a smart device 330 to the training module 310 for the purpose of implementing and communicating an individual training program and monitoring routine. The smart device 330 makes a wireless connection to the training module 310 through its transceiver (e.g., a WiFi-compatible transceiver, such as transceiver 230 in FIG. 4). Training routines may be initiated by either the smart device 330 or the training module 310, optionally displayed to the user 315 on the smart device 330, and monitored directly by the smart device 330 or training module 310. In the simplest case, a training routine may be initiated by simply starting a timer or pushing a reset button on either the training module 310 or the smart device 330. In further embodiments, the training routine may comprise a specific number, type, and/or sequence of compressions and rotations of the training module, optionally to be performed within a specified or predetermined time period. Such routines may be displayed to the user 315 on the smart device 330 as text, a table or chart, graphics, a combination thereof, etc.

When a training routine is initiated by the training module 310, the training routine (or alternatively, the start of data collection) may be transmitted to the smart device 330 for display to the user 315. The user can perform the training routine and get real-time feedback from the training module 310, which transmits the number and (optionally) the type of compressions and/or the number and (optionally) the type of rotations to the smart device 330 for further display to the user 315. Alternatively, the training routine may be initiated by the training module 310, and the results may be transmitted to the smart device 330 for display to the user 315.

Figure 6:
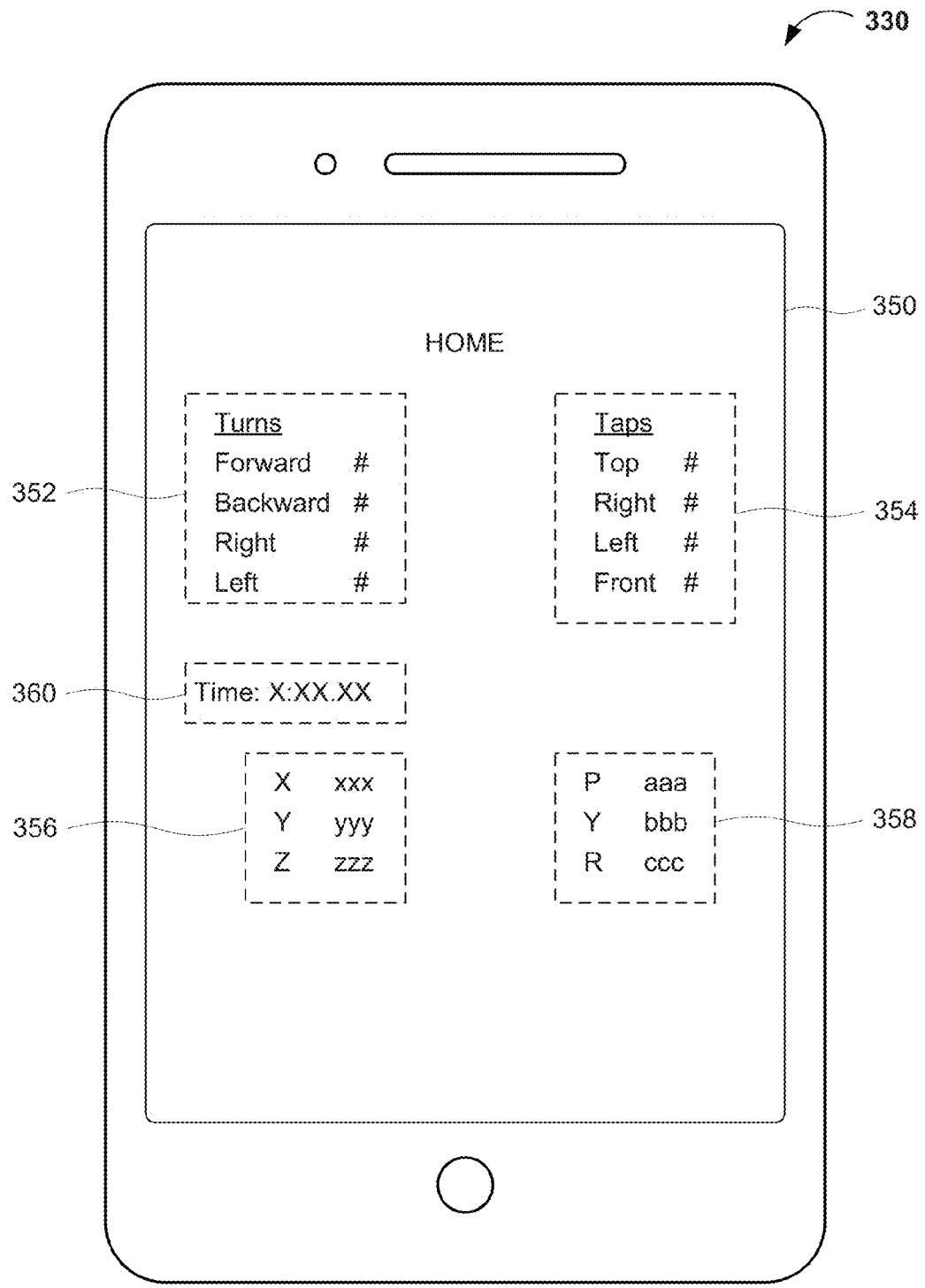
FIG. 6 shows an exemplary display on an exemplary mobile electronic device, displaying data relating to compressions and rotations of the present training module.

For example, FIG. 6 shows smart device 330 with a display are 350 showing results and/or performance of a training routine as tables or lists of data. For example, rotation data is displayed in region 352 ("Turns"), which displays both the type of rotations (e.g., Forward, Backward, Right, Left) and the number of each type of rotation. Compression data is displayed in region 354 ("Taps"), which displays both the type of compression (e.g., Top, Right, Left, Front) and the number of each type of compression. A real-time stopwatch function is displayed in region 360 ("Time"), preferably in minutes and seconds, and optionally, in tenths and/or hundredths of seconds.

Real-time position information from the motion detector (e.g., motion detector 220 in FIG. 4) in the training module may be displayed in regions 356 and 358. Region 356, for example, displays X, Y and Z (e.g., orthogonal linear dimension) data from at least 3 accelerometers in the training module as absolute numbers. The numbers may be on a scale of from −999 to 999, where 000 represents no movement from an initial position (e.g., immediately after a reset operation), and −999 and 999 represent linear movement of the training module of about, equal to or greater than several times the height, width or thickness of the training module in either direction along a given axis. In one example, the greatest value of the numbers representing linear movement of the training module is twice the height, width or thickness of the training module. In other examples, the greatest value of the numbers representing linear movement of the training module is about three or four times the height, width or thickness of the training module, or more, depending on the exercises in the training routine.

For example, downward compressions may be determined by tapping the top surface of the training module, comparing the number along the up-down linear axis (e.g., Y) to a threshold, and determining that a compression occurred when the number exceeds the threshold (and optionally returns to its original value or a value close to the original value). If we assume a 20 cm×20 cm×20 cm cubic training module and that compressions of 0.1 cm, 1 cm and 2 cm respectively result in changes in the value along the Y axis of 10, 50, and 150, then a threshold for determining a top compression can be set at 20. A tap by the user 315 on top of the training module resulting in a change in the Y axis value of more than 20, optionally followed by a return (typically within a relatively short period of time, such as 1 second) to a value less than 20 away from the original value, will be read as a top compression. One skilled in the art can program the controller in the training module to make such comparisons and report the results of such comparisons (via the signal transmitter in the training module) to an external device. Similar determinations can be made for right, left and front compressions, using different axes (e.g., X for right and left compressions, Z for front compressions). Furthermore, similar determinations can be made for exercises such as lifting or extending the training module, or for jumping with the training module held in the user's hands or between the user's knees or ankles, but on a differently-calibrated scale, and/or using different thresholds.

Similar determinations can also be made for rotations of the training module. In any rotation of the training module, the linear position data will change along at least one axis without going back to the original value. For example, assuming the 20 cm×20 cm×20 cm cubic training module, and linear changes of 2 cm, 4 cm and 8 cm respectively resulting in changes in the value along a linear axis of 150, 300, and 600, then a threshold for determining a rotation can be set at 300. For example, a rotation of the training module to the right by the user 315 resulting in a change in the X axis value of more than +300, optionally without a significant change in value or a return to a value close to the original value (typically within a relatively short period of time, such as 1 second), will be read as a right rotation. A similar rotation of the training module to the left by the user 315 resulting in a change in the X axis value of more than −300 will be read as a left rotation. Furthermore, when a given accelerometer is not in the center of the training module or under the center of a surface of the training module, the position of that accelerometer will change in at least two dimensions. Rotation determinations can be made with such accelerometers using two axes, without reference to the lack of any subsequent change in position (or return to the original position). One skilled in the art can program the controller in the training module to make such comparisons and report the results of such comparisons via the signal transmitter in the training module to an external device. Similar determinations can be made for front and back rotations, or double rotations (in one direction or more than one direction), or rotations along a direction not coincident with one of the linear axes, using different or multiple axes.

Similar determinations can be made for rotations of the training module using the rotational position data (e.g., pitch, yaw and roll) in region 358 (indicated by the initial letters P, Y and R, respectively). The values of the rotational position data may be given on a calibrated scale (e.g., from −999 to 999) or as real angle values. When the rotational position data in one or more planes exceeds a threshold value (e.g., 45° or equivalent to 45° for 90° rotations, 30° or equivalent to 30° for 60° rotations, etc.), a given rotation and rotation type can be determined. In some embodiments, compressions may not be determined using rotational position data.

Referring back to FIG. 5, in a further embodiment, a mobile computer 320 (e.g., accessible to and/or operated by the coach or instructor 325) may also connect to the access point (i.e., training module 310) and monitor the performance of the user 315 in the training routine. Any number of mobile electronic devices configured to communicate wirelessly with other devices using a known, commonly shared protocol may connect to the training module 310 (or, alternatively, to the smart device 330 or laptop computer 320) to monitor the individual's training routine.

The present network 300 advantageously avoids any requirement for a server computer to operate the training module 310, implement the training regimen, or collect or process compression and/or rotation data reported by the training module 310. A single smart device (e.g., smart device 330 or laptop computer 320) may connect to and monitor the data from the training module 310 and provide training routine prompts, resets, and/or instructions. In addition, any number of mobile devices may connect to the access point (e.g., the wireless signal transmitter) in the training module 310 and receive the training data from the module 310.

Figure 7:
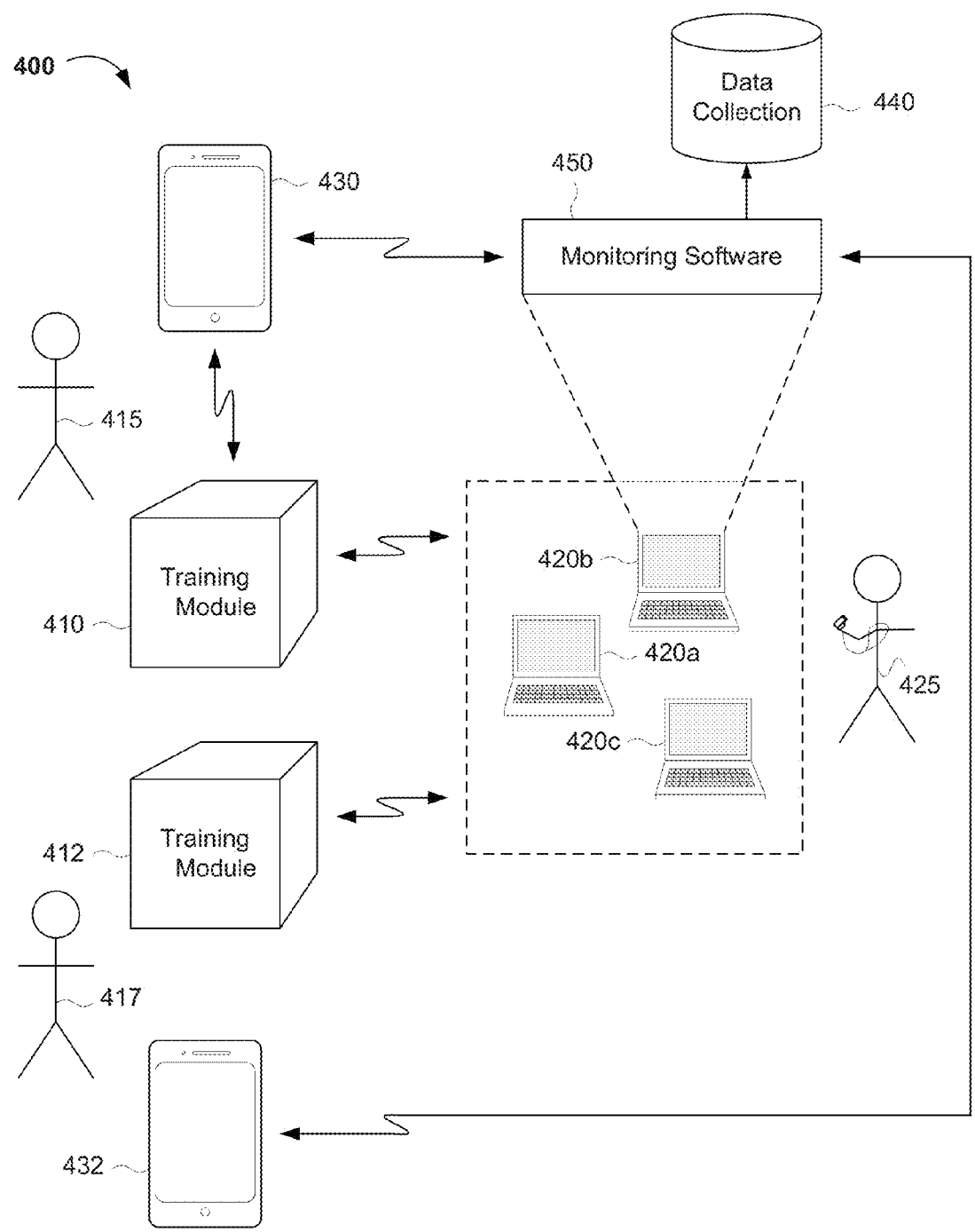
FIG. 7 shows another exemplary training system including multiple training modules, in accordance with a second embodiment of the present invention.

FIG. 7 shows a multi-user training network 400, in which training cubes 410 and 412 serve as network clients. The multi-user network 400 allows the training modules 410 and 412 to connect to an existing wireless (e.g., Wi-Fi) network. Once connected, the training modules 410 and 412 communicate with monitoring software 450 running on a computer (e.g., laptop 420b) on the network 400. The monitoring software 450 monitors and collects training data from all training monitors (e.g., 410 and 412) connected to the monitoring software 450, and the computer (e.g., laptop 420b) running the software 450 can store the training data in data collection memory 440 and/or re-transmit training information to all user clients (e.g., smart devices 430 and 432, and coach/instructor portable computers 420a and 420c) that are also connected to the network 400. In this configuration, training routines may be initiated by the monitoring software 450 or from the smart devices that are also connected indirectly to the monitoring software 450.

The multi-user training network 400 advantageously enables multiple (e.g., two or more) training modules to be monitored simultaneously by one or more user clients (e.g., all of the smart phones, laptops, tablet computers, etc.) connected to the computer 420b running the monitoring software 450, and any coach, instructor or user may initiate a training routine.

Exemplary Methods of Monitoring Physical Activity

In another aspect, the present invention concerns a method of monitoring physical activity, comprising instructing one or more users to tap and/or rotate an associated training module, collecting data relating to a number of compressions on a surface of the compressible article and/or a number of rotations of the compressible article, and displaying to the user on a mobile electronic device the number of compressions and the number of rotations of the compressible article. In general, the training module is associated with a unique user, and comprises a compressible article having a polyhedral outer surface, and a circuit comprising a motion detector, a controller, and a signal transmitter in the compressible article. The circuit is configured to detect compressive and rotational movement of the compressible article, determine a number of compressions and a number of rotations of the compressible article, and transmit data regarding the number of compressions and/or rotations of the compressible article. The controller is generally in electrical communication with the motion detector, and the signal transmitter is generally in electrical communication with the controller.

FIG. 8 is a flow chart 500, showing an exemplary method of monitoring physical activity. The method starts at 510, and at 520, provides instructions to one or more users for tapping and/or rotating a training module. Thus, in some embodiments, the method further comprises instructing a plurality of users to tap and/or rotate an associated training module. The instructions comprise or consist of a training regimen or routine, as described herein. The users may be instructed to perform part or all of the training regimen or routine within a certain period of time. When there are multiple users, the users may receive the same or different instructions.

In some embodiments, the user(s) are instructed to (i) tap the training module a first predetermined or minimum number of times and (ii) rotate the training module a second predetermined or minimum number of times. In further embodiments, the users may be instructed to tap a first surface (e.g., the top) of the training module the first number of times, rotate the training module in a first direction (e.g., to the right) the second number of times, rotate the training module in a second direction (e.g., to the left) a third predetermined or minimum number of times, optionally rotate the training module in a third direction (e.g., to the back or to the front) a fourth predetermined or minimum number of times, tap a second surface of the training module (e.g., the right or left surface) a fifth predetermined or minimum number of times, and/or tap a third surface of the training module (e.g., the other of the right or left surface) a sixth predetermined or minimum number of times. Thus, in some embodiments of the present method, the first surface of the training module is a top surface, the first direction is one panel or side of the polyhedral compressible article to the right, and the second direction is one panel or side of the polyhedral compressible article to the left.

In FIG. 8, at 530, the method determines whether a particular movement of the training module is a compression (e.g., an intentional tap with the user's foot) or rotation (e.g., an intentional turn of the training module). In some embodiments, when it is determined that a compression or rotation occurred, the number of compressions and/or rotations of the training module may be counted in the training module, as absolute numbers or over time. At 540, data relating to compression(s) and/or rotation(s) (or the number[s] of such compressions and/or rotations) is transmitted to one or more mobile display devices. In most embodiments, the data is transmitted wirelessly, but in some embodiments, the data may be transmitted over a wire electrically connecting the training module to the mobile display device(s). In general, the user's mobile display device receives such data. Optionally, the compression and/or rotation data is transmitted to other mobile display device(s) (e.g., accessible to or operated by one or more coaches and/or instructors). Thereafter, at 550, the data may be displayed on the mobile display device (e.g., of the user and/or of the coach and/or instructor), and optionally, on a signal processing device (e.g., operated by a coach or instructor). In embodiments involving multiple users, the number of compressions and the number of rotations of the compressible article associated with each of the users may be displayed to coaches the mobile electronic device associated with the user, and/or to other users, coaches and/or instructors, as desired, permitted authorized or needed.

In further embodiments, at 542, data relating to compression(s) and/or rotation(s) (or the number[s] of such compressions and/or rotations) is transmitted to one or more data processing devices (e.g., laptop computer 420b in FIG. 7, which executes monitoring software 450). Thus, the present method may further comprise transmitting data relating to the number of compressions on the surface of the compressible article and/or the number of rotations of the compressible article to a data processing device.

Referring back to FIG. 8, at 544, the data processing device(s) process and optionally store the data in a data storage unit (e.g., in data collection memory 440 in FIG. 7). In embodiments involving multiple users, the compression and rotation data from each of the plurality of training modules may be processed. Processing the data from the training module(s) may comprise calculating a rate of compressions and/or rotations, determining a maximum number of compressions and/or rotations, comparing the number or rate of compressions and/or rotations to a stored and/or threshold value, etc. The stored data may be unprocessed (e.g., received) data or processed data. In embodiments involving multiple users, transmitting, processing and/or storing the data may comprise collecting data relating to the number of compressions and/or the number of rotations from the various training modules in real time.

In FIG. 8, at 546, the stored and/or processed data is retrieved (e.g., from data collection memory 440 in FIG. 7) and transmitted to one or more mobile display devices (e.g., accessible to and/or operated by a user, coach, instructor, etc.). Optionally, at 548, the stored and/or processed data may be further processed by the signal processing device. Further processing the processed data may comprise, in addition to the data processing operations recited above, adding the processed data to one or more sets of stored data, calculating an average number and/or rate of compressions and/or rotations over a plurality of training routines or regimens, plotting one or more graphs of compression and/or rotation data from one or more training routines or regimens, compiling compression and/or rotation data from a plurality of users, etc.

As mentioned above, at 550, the method displays the (further) processed data on the mobile electronic device(s). The processed data is displayed on any or all displays receiving an output from the data processing device that processes the compression and rotation data. The mobile electronic device(s) include the user's smart phones and/or the portable computers of the coach(es) and/or instructor(s). Optionally, the (further) processed data is displayed on the data processing device (e.g., laptop computer 420b in FIG. 7 with monitoring software 450 installed thereon).

At 560, the training module may be reset. As described above, resetting the training module may comprise resetting the controller and/or erasing or resetting the random access memory. If the training module is reset, another training routine or regimen may be initiated, and the method returns to 520. If the training module is not reset, the training may be over, and the method may end at 570.

Exemplary Software for Monitoring Physical Activity

A further aspect of the invention relates to a computer program and/or software, implementable and/or executable in a general purpose computer or workstation or other electronic apparatus equipped with conventional digital and/or analog signal processor(s) (e.g., microprocessor, microcontroller, DSP, etc.), configured to perform one or more steps of the method and/or one or more operations of the hardware. Consequently, a further aspect of the invention relates to software that implements the above method. For example, the invention may further relate to software and/or a tangible computer-readable medium containing a set of instructions which, when executed by an appropriate signal processing apparatus, is configured to perform the method of monitoring physical activity described herein. The computer-readable medium may comprise any (tangible) medium that can be read by a signal processing apparatus configured to read the medium and execute code stored thereon or therein, such as a floppy disk, CD-ROM, magnetic tape or hard disk drive. Such code may comprise object code, source code, and/or binary code.

The code is generally configured for transmission through an appropriate medium, such as copper wire, a conventional network cable, a conventional optical data transmission cable, or even air or a vacuum (e.g., outer space) for wireless signal transmissions. The code is generally digital, and is generally configured for processing by a conventional digital data processor (e.g., a microprocessor, microcontroller, or logic circuit such as a programmable gate array, programmable logic circuit/apparatus or application-specific [integrated] circuit).

Specifically, in various exemplary embodiments, the method, and variations thereof, may be accomplished by a computer-readable medium comprising computer-executable instructions that is adapted to perform the various steps of the method. For example, the computer-executable instructions may be adapted to instruct one or more users to tap and/or rotate an associated training module, determine whether one or more movements of the compressible article along one or more orthogonal linear axes and/or in one or more orthogonal planes is a compression on a surface of the compressible article and/or a rotation of the compressible article, collect data relating to the number of compressions and/or rotations, and display to the user on a mobile electronic device the number of compressions and the number of rotations of the compressible article. The computer-executable instructions may be further adapted to modify device firmware to perform such steps. Additionally, the computer-executable instructions may also be adapted to provide instructions and/or compiled and/or processed data to a user interface. The computer-readable medium is generally stored in a hard drive or ROM on a data processing device (e.g., a laptop or tablet computer), or placed into an appropriate medium reader (e.g., CD-ROM reader, DVD reader, flash disk drive, etc.), and therefore be accessible to the data processing device, as shown in FIG. 7.

Thus, to help implement the present software and/or method of monitoring physical activity, the training module may further comprise one or more memories storing instructions to determine the number of compressions and the number of rotations of the compressible article, display the number of compressions and the number of rotations of the compressible article to the user on the mobile electronic device or a coach or instructor on a portable computer, and/or display commands or indications on the user's mobile electronic device to tap a surface of the training module and/or rotate the training module in a given or predetermined direction.

Exemplary Methods of Making an Automated Data-Reporting Training Module

The present invention further relates to method of making a training module, comprising electrically connecting a motion detector, a controller, and a signal transmitter; inserting the motion detector, the controller, and the signal transmitter in a compressible article; and closing or sealing the compressible article. The compressible article, which may define the outermost boundaries of the training module, generally has a polyhedral outer surface, as described herein. The motion detector is configured to detect compressive and rotational movement of a compressible article having a polyhedral outer surface. The controller is configured to determine a number of compressions and a number of rotations of the compressible article. The signal transmitter is configured to transmit data regarding the number of compressions and/or rotations of the compressible article. The method may further comprise inserting a battery into the compressible article, and connecting the battery to at least the controller. In many embodiments, the signal transmitter comprises a wireless signal transmitter.

FIG. 9 is a flow chart 600 showing an exemplary method of making a training module. The training module may automatically report data relating to the compressions and/or rotations of the training module to an external device (e.g., a mobile electronic device configured to display such data). The method may start at 610, and at 620, a motion detector, a controller, and a signal transmitter may be electrically connected such that the motion detector detects compressive and rotational movement of a compressible article, the controller determines a number of compressions and a number of rotations of the compressible article, and the signal transmitter transmits data regarding the number of compressions and/or rotations of the compressible article. The motion detector, controller, and signal transmitter may be mounted onto a circuit board having metal traces thereon, adapted to make electrical connections between certain inputs and/or outputs of the motion detector, controller, and signal transmitter. In further embodiments, other components, such as a switch, an activity indicator, etc., may be electrically connected to one or more components in the electronic circuitry, such as the controller, the battery (when present), etc., as described herein. The method may further comprise placing, enclosing, or encasing the motion detector, controller, and signal transmitter (or a circuit board on which these components are mounted and wired to each other) in a housing, for security and/or protection of the electrical components. In such an embodiment, the method may further comprise feeding or placing wires from the components in the housing (e.g., the controller) through the housing and connecting the wires to a battery and/or switch outside the housing, as described herein.

Next, at 630, the electrically-connected motion detector, controller, and signal transmitter (or circuit board containing the same) is inserted into a polyhedral compressible article that forms the outer boundary or shell of the training module. Thus, the polyhedral compressible article may have a cavity therein in which the motion detector, controller, and signal transmitter (or circuit board) are placed or mounted. In one embodiment, when the motion detector, controller, and signal transmitter (or circuit board) are enclosed or encased in a housing, the cavity may have dimensions similar or substantially equal to the housing.

At 640, the polyhedral compressible article is closed or sealed. Thus, steps 630 and 640 may comprise removing a side or portion of a side of the polyhedral compressible article to expose a cavity in the polyhedral compressible article, inserting the electrical components into the polyhedral compressible article, placing the removed side or portion of the polyhedral compressible article back onto the polyhedral compressible article, and sealing the polyhedral compressible article. The removed side or portion of the polyhedral compressible article may be sealed with an adhesive (e.g., epoxy, hot melt glue, etc.), tape, thermal energy and pressure (e.g., when the polyhedral compressible article comprises a thermoelastic polymer foam), etc. Alternatively, the removed side or portion of the polyhedral compressible article may have projections (e.g., one or more tongues, teeth or joints) or depressions (e.g., one or more grooves or notches), and the remaining compressible article may have complementary fittings configured to make a tight fit when the removed side or portion is placed back onto the polyhedral compressible article.

In further embodiments, the method of making an automatic data-reporting training module may comprise programming the training module (e.g., the controller or memory in the controller) to perform one or more steps of the present method of monitoring a training regimen or routine, calibrating the training module (e.g., the motion detector) to reliably determine compressions and rotations of the training module or compressible article, and/or configuring the training module to communicate with one or more other devices in a wireless network. At 650, the method ends.

A number of embodiments have been described. Nevertheless, it will be understood that various modifications may be made without departing from the spirit and scope of the invention.

CONCLUSION/SUMMARY

Thus, embodiments of the present invention relate to a training module, a training system, and methods of monitoring physical activity and making a training module. The training module generally comprises a compressible article having a polyhedral outer surface, and a motion detector, a controller, and a signal transmitter in the compressible article. The motion detector generally detects compressive and rotational movement of the compressible article. The controller is in electrical communication with the motion detector, and generally determines a number of compressions and a number of rotations of the compressible article. The signal transmitter is in electrical communication with the controller, and generally transmits data (e.g., to a mobile electronic device or other signal receiving and/or stat processing device in a network) regarding the number of compressions and/or rotations of the compressible article. The present invention can advantageously improve the user's agility, endurance, speed, reflexes, and/or sensitivity, give real-time feedback on and historical analysis of the user's performance, and provide coaches and/or instructors with real-time and historical performance data for each member of a group, while at the same time increase or maximize safety for the users during training in a group activity that might otherwise involve use of one or more spherical objects. The present training module, system and methods can be used indoors and outdoors, and on a variety of ground and floor surfaces.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A training module, comprising:
   a) a compressible article having a polyhedral outer surface;
   b) a motion detector in the compressible article, configured to detect compressive and rotational movement of the compressible article;
   c) a controller in the compressible article, in electrical communication with the motion detector, configured to determine a number of compressions and a number of rotations of the compressible article; and
   d) a signal transmitter in the compressible article, in electrical communication with the controller, the signal transmitter configured to transmit data regarding the number of compressions and/or rotations of the compressible article.

2. The training module of claim 1, wherein said motion detector comprises an accelerometer and/or a gyroscope in communication with said controller, and optionally, one or more pressure sensors in electrical communication with said controller.

3. The training module of claim 1, wherein the signal transmitter comprises a wireless signal transmitter and an antenna.

4. The training module of claim 1, further comprising:
   a) a battery providing electrical power to said controller, said motion detector, and said signal transmitter;
   b) a switch configured to disconnect said battery from said controller; and
   c) an optional activity monitor configured to indicate when said motion detector and/or said signal transmitter are active.

5. The training module of claim 1, wherein said controller comprises:
   a signal processor configured to communicate electrically with said motion detector and said signal transmitter;
   one or more memories configured to store instructions and/or data; and
   a clock circuit configured to provide a timing signal to said signal processor and optionally to at least one of said one or more memories.

6. The training module of claim 5, wherein said controller further comprises a reset circuit configured to reset said signal processor and optionally at least one of said one or more memories.

7. The training module of claim 5, wherein said one or more memories stores an instruction set configured to:
   determine whether a movement of said motion sensor in one dimension is a compression on a top surface or on one of at least two side surfaces of said compressible article;
   determine whether a movement of said motion sensor in two dimensions is a rotation of the compressible article; and
   transmit a data signal to an external electronic device when said compression or said rotation occurs.

8. The training module of claim 1, wherein said polyhedral outer surface has a shape of a regular polyhedron having at most 12 sides.

9. A training system, comprising:
   a) training module of claim 1; and
   b) a mobile electronic device, configured to display a number of compressions and a number of rotations of the compressible article.

10. The training system of claim 9, further comprising a data storage unit configured to store compression and rotation data from the training module, and a computer configured to process said compression and rotation data and display information relating to one or more summaries of and/or trends in said compression and rotation data.

11. The training system of claim 10, further comprising a second training module and a second mobile electronic device, wherein said computer is capable of (i) simultaneously receiving data from said first and second training modules in real time and (ii) processing said compression and rotation data from each of said first and second training modules.

12. A method of monitoring physical activity, comprising:
   a) instructing one or more users to tap and/or rotate a training module associated with a unique user, the training module comprising:
      i) a compressible article having a polyhedral outer surface;
      ii) a motion detector in the compressible article, configured to detect compressive and rotational movement of the compressible article;
      iii) a controller in the compressible article, in electrical communication with the motion detector, configured to determine a number of compressions and a number of rotations of the compressible article; and
      iv) a signal transmitter in the compressible article, in electrical communication with the controller, the signal transmitter configured to transmit data regarding the number of compressions and/or rotations of the compressible article;
   b) collecting data relating to a number of compressions on a surface of the compressible article and/or a number of rotations of the compressible article; and
   c) displaying to said user on a mobile electronic device the number of compressions and the number of rotations of the compressible article.

13. The method of claim 12, wherein said user is instructed to (i) tap said training module a first predetermined or minimum number of times and (ii) rotate said training module a second predetermined or minimum number of times, all within a predetermined period of time.

14. The method of claim 13, wherein said user is instructed to:
   a) tap a first surface of said training module the first predetermined or minimum number of times;
   b) rotate said training module in a first direction the second predetermined or minimum number of times;
   c) rotate said training module in a second direction a third predetermined or minimum number of times;
   d) optionally tap a second surface of said training module a fourth predetermined or minimum number of times;
   e) optionally tap a third surface of said training module a fifth predetermined or minimum number of times; and
   f) optionally rotate said training module in a third direction a sixth predetermined or minimum number of times.

15. The method of claim 14, wherein the training module further comprises one or more memories storing instructions to:
   a) determine the number of compressions and the number of rotations of the compressible article; and
   b) display the number of compressions and the number of rotations of the compressible article to said user on said mobile electronic device; and
   c) optionally display commands or indications on said mobile electronic device to tap said first surface of said training module and/or rotate said training module.

16. The method of claim 14, wherein said first surface of said training module is a top surface, said first direction is one panel or side of the polyhedral compressible article to the right, and said second direction is one panel or side of the polyhedral compressible article to the left.

17. The method of claim 12, further comprising transmitting said data relating to said number of compressions on said surface of the compressible article and/or said number of rotations of the compressible article to a data processing device, wherein said data processing device processes said data and stores said processed data in a data storage unit, and optionally, retrieving said processed data from said data storage unit, optionally further processing said processed data and displaying said (further) processed data on said mobile electronic device.

18. The method of claim 17, further comprising
   a) instructing a plurality of users to tap and/or rotate an associated training module;
   b) collecting data relating to the number of compressions and/or the number of rotations from said associated training modules in real time;
   c) displaying to each of said users on an associated mobile electronic device the number of compressions and the number of rotations of the associated compressible article;
   d) processing said compression and rotation data from each of said plurality of training modules; and
   e) displaying said processed data on a display receiving an output from a processing device that processes said compression and rotation data.

19. A method of making a training module, comprising:
   a) electrically connecting a motion detector, a controller, and a signal transmitter and such that said motion detector is configured to detect compressive and rotational movement of a compressible article having a polyhedral outer surface, the controller is configured to determine a number of compressions and a number of rotations of the compressible article, and the signal transmitter is configured to transmit data regarding the number of compressions and/or rotations of the compressible article;
   b) inserting the motion detector, the controller, and the signal transmitter in the compressible article; and
   c) closing or sealing the compressible article.

20. The method of claim 19, further comprising inserting a battery into the compressible article and connecting said battery to at least said controller, wherein said signal transmitter comprises a wireless signal transmitter.

* * * * *